(12) United States Patent
Scheidel et al.

(10) Patent No.: US 7,541,486 B2
(45) Date of Patent: *Jun. 2, 2009

(54) METHOD FOR PRODUCING 3-PENTENENITRILE

(75) Inventors: Jens Scheidel, Hirschberg (DE); Tim Jungkamp, Kapellen (BE); Michael Bartsch, Neustadt (DE); Gerd Haderlein, Grünstadt (DE); Robert Baumann, Mannheim (DE); Hermann Luyken, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 379 days.

This patent is subject to a terminal disclaimer.

(21) Appl. No.: 10/586,007

(22) PCT Filed: Jan. 27, 2005

(86) PCT No.: PCT/EP2005/000774

§ 371 (c)(1),
(2), (4) Date: Jul. 12, 2006

(87) PCT Pub. No.: WO2005/073171

PCT Pub. Date: Aug. 11, 2005

(65) Prior Publication Data

US 2008/0227998 A1    Sep. 18, 2008

(30) Foreign Application Priority Data

Jan. 29, 2004   (DE) ...................... 10 2004 004 720

(51) Int. Cl.
*C07C 255/00* (2006.01)
*C07C 253/00* (2006.01)

(52) U.S. Cl. ...................... 558/465; 558/303; 558/332; 558/435; 558/462; 558/463

(58) Field of Classification Search ................ 558/335, 558/338, 355, 356, 303, 332, 435, 462, 463, 558/465

See application file for complete search history.

(56) References Cited

U.S. PATENT DOCUMENTS

| 3,496,215 | A |   | 2/1970 | Drinkard et al. |
| 3,773,809 | A |   | 11/1973 | Walter |
| 4,810,815 | A |   | 3/1989 | Bryndza |
| 5,693,843 | A |   | 12/1997 | Breikss et al. |
| 5,696,280 | A |   | 12/1997 | Shapiro |
| 5,821,378 | A |   | 10/1998 | Foo et al. |
| 5,981,772 | A |   | 11/1999 | Foo et al. |
| 6,197,992 | B1 |   | 3/2001 | Fischer et al. |
| 7,439,381 | B2 | * | 10/2008 | Jungkamp et al. ........... 558/322 |

FOREIGN PATENT DOCUMENTS

DE          196 52 273          6/1998

OTHER PUBLICATIONS

Tolman et al., "Homogeneous Nickel-Catalyzed Olefin Hydrocyanation", Advances in Catalysis 33 (1985), pp. 1-46.
Keese, R. et al., "Distillation", Fundamentals of Preparative Organic Chemistry (1982), pp. 26-33.

* cited by examiner

*Primary Examiner*—Kamal A Saeed
*Assistant Examiner*—Samantha L Shterengarts
(74) *Attorney, Agent, or Firm*—Connolly Bove Lodge & Hutz

(57) ABSTRACT

A process is described for preparing 3-pentenenitrile, characterized by the following process steps:
(a) reacting 1,3-butadiene with hydrogen cyanide over at least one catalyst to obtain a stream 1 which comprises 3-pentenenitrile, 2-methyl-3-butenenitrile, the at least one catalyst and 1,3-butadiene,
(b) distilling stream 1 in a column to obtain a high-1,3-butadiene stream 2 as the top product and a low-1,3-butadiene stream 3 as the bottom product which comprises 3-pentenenitrile, the at least one catalyst and 2-methyl-3-butenenitrile,
(c) distilling stream 3 in a column to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst,
(d) distilling stream 5 to obtain a stream 7 as the top product which comprises 2-methyl-3-butenenitrile, and a stream 8 as the bottom product which comprises 3-pentenenitrile.

20 Claims, 6 Drawing Sheets

METHOD FOR PRODUCING 3-PENTENENITRILE

RELATED APPLICATIONS

This application is a national stage application (under 35 U.S.C. 371) of PCT/EP2005/000774 filed Jan. 27, 2005, which claims benefit of German application 10 2004 004 720.0 filed Jan. 29, 2004.

BACKGROUND OF THE INVENTION

1. Field of the Invention

The present invention relates to a process for preparing 3-pentenenitrile.

2. Description of Related Art

Adiponitrile is an important starting material in nylon production and is obtained by double hydrocyanation of 1,3-butadiene. In a first hydrocyanation, 1,3-butadiene is hydrocyanated to 3-pentenenitrile, and the by-products obtained are mainly 2-methyl-3-butenenitrile, 4-pentenenitrile, 2-pentenenitriles, 2-methyl-2-butenenitriles, $C_9$ nitriles and methylglutaronitrile. In a second, subsequent hydrocyanation, 3-pentenenitrile is reacted with hydrogen cyanide to give adiponitrile. Both hydrocyanations are catalyzed by nickel (0)-phosphorus complexes.

For the second hydrocyanation, it is essential that the 3-pentenenitrile used is free of 2-methyl-3-butenenitrile, since 2-methyl-3-butenenitrile is otherwise hydrocyanated to the undesired by-product methylglutaronitrile.

A general review of nickel-catalyzed olefin hydrocyanation is given in Tolman et al., Adv. Cat. 33, 1-46 (1985).

The hydrocyanation of 1,3-butadiene using a nickel catalyst of the formula $Ni[P(OR)_3]_4$ is described in U.S. Pat. No. 3,496,215. A disadvantage of this process is that no suitable technique for fully recovering the 1,3-butadiene or the catalyst is specified.

U.S. Pats. No. 5,693,843, 5,696,280, 5,821,378 and 5,981,772 describe hydrocyanations of 1,3-butadiene with multidentate phosphorus ligands, although no suitable procedure for the recovery of the catalyst components is shown in the individual embodiments.

The performance of the hydrocyanation in one or more reactors and their connection is described in U.S. Pat. No. 4,810,815, and the possibility is mentioned of continuous operation of stirred tanks or batteries of stirred tanks, but only a semibatch mode is described in detail in examples, from which it cannot be directly discerned by those skilled in the art under which conditions the method has to proceed in continuous stirred tanks.

A process for removing organic phosphorus compounds and their metal complexes from organic nitriles in the hydrocyanation of olefins is described in U.S. Pat. No. 3,773,809. The removal is effected by contacting the product with a cycloparaffin or a paraffinic hydrocarbon. This forms a liquid multiphasic system. This method of removing and recovering catalyst components by extraction cannot be applied in the hydrocyanation of 1,3-butadiene owing to the concentration of dinitriles in the reaction product being too low.

BRIEF SUMMARY OF THE INVENTION

It is thus an object of the present invention to provide an integrated process for preparing 3-pentenenitrile by hydrocyanation of 1,3-butadiene, in which 3-pentenenitrile is obtained substantially free of 2-methyl-3-butenenitrile, the 1,3-butadiene used is preferably recycled to increase the process yield and the catalyst is preferably removed from the pentenenitriles and recycled for the purposes of its economic use.

It is known that 2-methyl-3-butenenitrile reacts to give methylglutaronitrile under the hydrocyanation conditions, especially in the presence of nickel(0) complexes. It is therefore a further object of the present invention to provide a process for preparing 3-pentenenitrile by hydrocyanation of 1,3-butadiene, in which preferably very little 2-methyl-3-butenenitrile is recycled into the hydrocyanation. Therefore, the recycled catalyst stream and the recycled portion of the 1,3-butadiene should be very substantially freed of 2-methyl-3-butenenitrile in the process according to the invention.

Furthermore, homogeneously dissolved hydrocyanation catalysts are known to be thermally labile. It is therefore a further object of the present invention to provide a process for preparing 3-pentenenitrile by hydrocyanating 1,3-butadiene, in which the catalyst is exposed preferably to very low thermal stress.

DETAILED DESCRIPTION OF THE INVENTION

Figure 1:
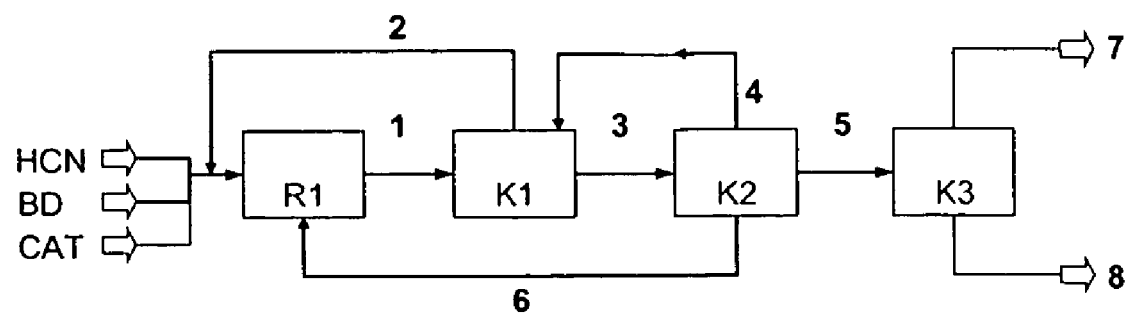
FIGS. 1-6 schematically illustrate various practices of this invention.

According to the invention, this object is achieved by a process for preparing 3-pentenenitrile.

The process according to the invention is characterized by the following process steps:

(a) reacting 1,3-butadiene with hydrogen cyanide over at least one catalyst to obtain a stream 1 which comprises 3-pentenenitrile, 2-methyl-3-butenenitrile, the at least one catalyst and 1,3-butadiene, (b) distilling stream 1 in a column to obtain a high-1,3-butadiene stream 2 as the top product and a low-1,3-butadiene stream 3 as the bottom product which comprises 3-pentenenitrile, the at least one catalyst and 2-methyl-3-butenenitrile, (c) distilling stream 3 in a column to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst, (d) distilling stream 5 to obtain a stream 7 as the top product which comprises 2-methyl-3-butenenitrile, and a stream 8 as the bottom product which comprises 3-pentenenitrile.

Process step (a) comprises the reaction of 1,3-butadiene with hydrogen cyanide over at least one catalyst. The catalysts used are nickel(0) catalyst complexes.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I

$$P(X^1R^1)(X^2R^2)(X^3R^3) \qquad (I)$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1 R^2 R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified in this description.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified in this description.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia

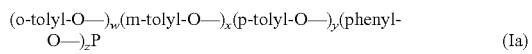

$$(\text{o-tolyl-O---})_w(\text{m-tolyl-O---})_x(\text{p-tolyl-O---})_y(\text{phenyl-O---})_z P \quad (\text{Ia})$$

where w, x, y, z are each a natural number, and the following conditions apply: $w+x+y+z=3$ and $w, z \leq 2$.

Such compounds Ia are, for example, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula Ib:

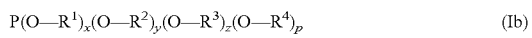

$$P(O-R^1)_x(O-R^2)_y(O-R^3)_z(O-R^4)_p \quad (\text{Ib})$$

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that $x+y+z+p=3$.

Preferred phosphites of the formula Ib can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound Ib, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula Ib are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula Ib are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula Ib may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula Ib.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites Ib and for the workup can be taken from DE-A 199 53 058.

The phosphites Ib may also be used in the form of a mixture of different phosphites Ib as a ligand. Such a mixture may be obtained, for example, in the preparation of the phosphites Ib.

However, preference is given to the phosphorus ligand being multidentate, in particular bidentate. The ligand used therefore preferably has the formula II

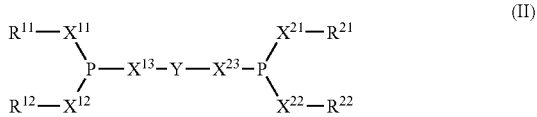

(II)

where $X^{11}, X^{12}, X^{13}, X^{21}, X^{22}, X^{23}$ are each independently oxygen or a single bond $R^{11}, R^{12}$ are each independently identical or different, separate or bridged organic radicals $R^{21}, R^{22}$ are each independently identical or different, separate or bridged organic radicals, Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals too may each be separate or bridged. The $R^{11}, R^{12}, R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003, which has an earlier priority date but had not been published at the priority date of the present application.

The compounds I, Ia, Ib and II described and their preparation are known per se. Phosphorus ligands used may also be a mixture comprising at least two of the compounds I, Ia, Ib and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula Ib $$P(O-R^1)_x(O-R^2)_y(O-R^3)_z(O-R^4)_p \qquad (Ib)$$

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

Process step (a) of the process according to the invention may be carried out in any suitable apparatus known to those skilled in the art. Useful apparatus for the reaction is that which is customary for this purpose, as described, for example, in: Kirk-Othmer, Encyclopedia of Chemical Technology, 4th Ed. Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, advantageous reactors have been found to be reactors having backmixing characteristics or batteries of reactors having backmixing characteristics. It has been found that batteries of reactors having backmixing characteristics which are operated in crossflow mode with regard to the metering of hydrogen cyanide are particularly advantageous.

The hydrocyanation may be carried out in the presence or in the absence of a solvent. When a solvent is used, the solvent should be liquid at the given reaction temperature and the given reaction pressure and inert toward the unsaturated compounds and the at least one catalyst. In general, the solvents used are hydrocarbons, for example benzene or xylene, or nitriles, for example acetonitrile or benzonitrile. However, preference is given to using a ligand as the solvent.

The reaction may be carried out in batch mode, continuously or in semibatch operation.

The hydrocyanation reaction may be carried out by charging the apparatus with all reactants. However, it is preferred when the apparatus is filled with the catalyst, the unsaturated organic compound and, if appropriate, the solvent. The gaseous hydrogen cyanide preferably floats over the surface of the reaction mixture or is passed through the reaction mixture. A further procedure for charging the apparatus is the filling of the apparatus with the catalyst, hydrogen cyanide and, if appropriate, the solvent, and slowly metering the unsaturated compound into the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

Preference is given to carrying out the hydrocyanation continuously in one or more stirred process steps. When a multitude of process steps is used, preference is given to the process steps being connected in series. In this case, the product is transferred from one process step directly into the next process step. The hydrogen cyanide may be fed directly into the first process step or between the individual process steps.

When the process according to the invention is carried out in semibatch operation, preference is given to initially charging the catalyst components and 1,3-butadiene in the reactor, while hydrogen cyanide is metered into the reaction mixture over the reaction time.

The reaction is preferably carried out at absolute pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, in each case per reactor.

In one embodiment, the reaction may be performed in the liquid phase in the presence of a gas phase and, if appropriate, of a solid suspended phase. The starting materials, hydrogen cyanide and 1,3-butadiene, may each be metered in in liquid or gaseous form.

In a further embodiment, the reaction may be carried out in liquid phase, in which case the pressure in the reactor is such that all feedstocks such as 1,3-butadiene, hydrogen cyanide and the at least one catalyst are metered in in liquid form and are in the liquid phase in the reaction mixture. A solid suspended phase may be present in the reaction mixture and may also be metered in together with the at least one catalyst, for example consisting of degradation products of the catalyst system comprising nickel(II) compounds inter alia.

In process step (a), a stream 1 is obtained which comprises 3-pentenenitrile, 2-methyl-3-butenenitrile, the at least one catalyst and unconverted 1,3-butadiene, and also residues of unconverted hydrogen cyanide. This stream 1 preferably has the following composition: from 1 to 80% by weight, more preferably from 5 to 50% by weight, of the at least one catalyst, from 0.1 to 50% by weight, more preferably from 1 to 25% by weight, of 1,3-butadiene, from 1 to 80% by weight, more preferably from 10 to 50% by weight, of pentenenitriles comprising trans-3-pentenenitrile, 2-methyl-3-butenenitrile and also further pentenenitrile isomers, and from 0.1 ppm by weight to 10% by weight, more preferably from 10 ppm by weight to 1% by weight, of hydrogen cyanide, based in each case on the overall composition of stream 1.

Stream 1 which comprises 3-pentenenitrile, 2-methyl-3-butenenitrile, the at least one catalyst and unconverted 1,3-butadiene is subsequently transferred into a distillation apparatus in process step (b). In this distillation apparatus, stream 1 is distilled to obtain a high-1,3-butadiene stream 2 as the top product and a low-1,3-butadiene stream 3 as the bottom product which comprises 3-pentenenitrile, the at least one catalyst and 2-methyl-3-butenenitrile.

Process step (b) of the process according to the invention may be carried out in in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in a single apparatus.

In a preferred embodiment of the process according to the invention, column internals having structured packing are present in the distillation apparatus and preferably generate between 2 and 60, more preferably between 3 and 40, in particular between 4 and 20, separation stages.

In a particularly preferred embodiment of the process according to the invention, the at least one evaporator stage associated with the distillation apparatus of process step (b) is designed in such a way that the material to be evaporated is subject to very little thermal damage, as achieved, for example, by falling-film evaporators, multiphase helical tube evaporators, thin-film evaporators or short-path evaporators by short contact times of the material on the evaporator surface and very low temperatures of the evaporator surfaces.

In a preferred embodiment of the process according to the invention, the distillation apparatus of process step (b) is operated with a divided bottom, in which case a circulation stream which is generally several times larger than stream 3 is conducted from a first column bottom of the distillation column in question to the evaporator, but the liquid effluent stream from the evaporator is not returned directly to the first column bottom and instead collected in a second column bottom which is separate from the first column bottom, stream 3 is obtained from the second column bottom and the remaining excess of evaporator circulation stream is allowed to overflow into the first column bottom to obtain, as stream 3 from the second column bottom, a mixture which is depleted in low boilers compared to the evaporator circulation stream drawn off from the first column bottom. The evaporator used is preferably a falling-film evaporator.

In a further preferred embodiment of the process according to the invention, the distillation is carried out at average residence times of the liquid phase in the bottom region of the one or more distillation apparatuses of together less than 10 hours, more preferably less than 5 hours, in particular less than 1 hour.

In a further preferred embodiment of the process according to the invention, the condensation at the top of the distillation apparatus is carried out in such a way that a substream of the top effluent is flushed back into the condenser.

In a further preferred embodiment of the process according to the invention, the distillation may be performed with a direct condenser, so that the condensation is carried out in a column section which is preferably equipped with a structured column packing, a collecting cup below this packing, a liquid draw from the collecting cup, a pumped circulation system, attached to the liquid draw, having a pump and heat exchanger, and also at least one apparatus for applying the liquid stream pumped in circulation to the packing above the collecting cup.

In order to achieve a very high process yield with respect to 1,3-butadiene in spite of the only partial conversion in step (a), preference is given to recycling the high-1,3-butadiene stream 2 into process step (a). The recycling of stream 2 into process step (a) may, if desired, also only be partial.

In a further embodiment, in the distillation of step (b), the 1,3-butadiene additionally required for the reaction in process step (a) may be added to the top region of the column or to stream 2.

In a further embodiment, the 1,3-butadiene added comprises a stabilizer, such as tert-butylpyrocatechol or 2,6-di-tert-butyl-para-cresol, according to the description in "Ullmann's Encyclopedia Of Industrial Chemistry, 6th Edition, 2000 Electronic Release, chapter "Butadiene—6. Stabilization, Storage and Transportation".

In a particularly preferred embodiment of the process according to the invention, the 1,3-butadiene either used directly in process step (a) or added to step (b) and transferred via stream 2 to step (a) is freed of water and, where present, the stabilizer by contacting with molecular sieve having a pore size less than 10 aÅngström or by contacting with alumina.

In a further particularly preferred embodiment, the 1,3-butadiene used directly in process step (a) or fed into stream 2 is used without stabilizer, in which case suitable selection of the pressure conditions keeps the condensation temperature in the top region of the distillation apparatus of process step (b) less than 293 K in order to prevent polymerization of 1,3-butadiene, especially in order to restrict the growth of popcorn polymer seeds.

The absolute pressure in process step (b) is preferably from 0.001 to 100 bar, more preferably from 0.01 to 10 bar, in particular from 0.5 to 5 bar. The distillation is carried out in such a way that the temperature in the bottom of the distillation apparatus is preferably from 30 to 140° C., more preferably from 50 to 130° C., in particular from 60 to 120° C. The distillation is carried out in such a way that the condensation temperature at the top of the distillation apparatus is preferably from −50 to 140° C., more preferably from −15 to 60° C., in particular from 5 to 45° C. In a particularly preferred embodiment of the process according to the invention, the aforementioned temperature ranges are maintained both at the top and in the bottom of the distillation apparatus.

The reflux ratio at the top of the distillation apparatus is preferably adjusted in such a way that stream 2 contains from 1 to 1000 ppm, more preferably from 5 to 500 ppm, in particular from 10 to 200 ppm, of 2 methyl-3-butenenitrile.

This contributes to the recycled 1,3-butadiene containing little 2-methyl-3-butenenitrile which reacts in process step (a) to give methylglutaronitrile.

In process step (b), a high-1,3-butadiene stream 2 is obtained as the top product and a low-1,3-butadiene stream 3 as the bottom product. The designation of the streams as high-1,3-butadiene or low-1,3-butadiene is based on the content of 1,3-butadiene of the stream 1 used in process step (b).

In a preferred embodiment of the process according to the invention, the high-1,3-butadiene stream 2 contains a total of from 50 to 100% by weight, more preferably from 80 to 100% by weight, in particular from 85 to 99% by weight, of 1,3-butadiene and butene isomers, and also a total of from 0 to 50% by weight, more preferably from 0 to 20% by weight, in particular from 10 ppm by weight to 1% by weight, of pentenenitrile isomers, of which substantially 2-methyl-3-butenenitrile and trans-3-pentenenitrile are present in stream 2.

In a preferred embodiment of the process according to the invention, the low-1,3-butadiene stream 3 contains a total of from 0 to 50% by weight, more preferably from 1 to 30% by weight, in particular from 2 to 20% by weight, of 1,3-butadiene and butene isomers, based in each case on the overall composition of stream 3. In a particularly preferred embodiment of the process according to the invention, the aforementioned specifications of 1,3-butadiene are achieved both in stream 2 and in stream 3.

The low-1,3-butadiene stream 3 stemming from process step (b) and comprising 3-pentenenitrile, the at least one catalyst and 2-methyl-3-butenenitrile is subsequently transferred to a distillation apparatus in process step (c). In this distillation apparatus, stream 3 is distilled to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst.

Process step (c) of the process according to the invention may be carried out in any suitable apparatus known to those skilled in the art. Suitable apparatus for this distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in one apparatus.

In a particularly preferred embodiment, the distillation apparatus in process step (c) comprises at least one distillation column having a stripping section. Especially preferred is an embodiment which comprises, as the distillation apparatus in process step (c), only one distillation column which is operated in stripping mode.

The distillation column in the distillation apparatus is preferably equipped with a structured packing which generates from 2 to 50, more preferably from 3 to 40, in particular from 4 to 30, theoretical plates.

In a particularly preferred embodiment of the process according to the invention, the at least one evaporator stages associated with the distillation apparatus of process step (c) are designed in such a way that the material to be evaporated is subject to very little thermal damage, as achieved, for example, by falling-film evaporators, multiphase helical tube evaporators, thin-film evaporators or short-path evaporators by short contact times of the material on the evaporator surface and very low temperatures of the evaporator surfaces.

The absolute pressure in process step (c) is preferably from 0.001 to 10 bar, more preferably from 0.010 to 1 bar, in particular from 0.02 to 0.5 bar. The distillation is carried out in such a way that the temperature in the bottom of the distillation apparatus is preferably from 30 to 140° C., more preferably from 50 to 130° C., in particular from 60 to 120° C. The distillation is carried out in such a way that the condensation temperature at the top of the distillation apparatus is preferably from −50 to 140° C., more preferably from −15 to 60° C., in particular from 5 to 45° C. In a particularly preferred embodiment of the process according to the invention, the aforementioned temperature ranges are maintained both at the top and in the bottom of the distillation apparatus.

In a further preferred embodiment of the process according to the invention, a bottom temperature of 140° C. is thus not exceeded in process steps (b) and (c).

In a further preferred embodiment of the process according to the invention, the distillation is carried out at average residence times of the liquid phase in the bottom region of the one or more distillation apparatuses of together less than 10 hours, more preferably less than 5 hours, in particular less than 1 hour.

In a particularly preferred embodiment of the process according to the invention, the distillation is carried out at average residence times of the liquid phase in the bottom region of all distillation apparatus in process steps (b) and (c) of together less than 10 hours, more preferably less than 5 hours, in particular less than 1 hour.

In the distillation of process step (c), a stream 4 is obtained as the top product. This stream 4 preferably contains a total of from 50 to 100% by weight, more preferably from 80 to 100% by weight, in particular from 90 to 99.9% by weight, of 1,3-butadiene and butene isomers, and also a total of from 0 to 50% by weight, more preferably from 0 to 20% by weight, in particular from 10 ppm by weight to 10% by weight, of pentenenitrile isomers, of which substantially 2-methyl-3-butenenitrile and trans-3-pentenenitrile are present in stream 4.

In a preferred embodiment of the process according to the invention, stream 4 is obtained in gaseous form in at least one condenser at the top of the distillation apparatus, and pentenenitrile components from the vapor stream of the distillation apparatus of process step (c) are at least partly condensed out in the at least one condenser in the abovementioned range of condensation conditions such as pressure and temperature, and recycled into the column at least partly in liquid form as a stream comprising pentenenitriles and also 1,3-butadiene and butene isomers.

In order to increase the process yield of 1,3-butadiene used in the process according to the invention, preference is given to recycling stream 4 into process step (a). The recycling of stream 4 into process step (a) may, if appropriate, also only be partial. Before it is recycled, stream 4 may additionally be subjected to an operation for the purposes of the process, for example a compression to a higher pressure.

In a particularly preferred embodiment of the process according to the invention, stream 4 is recycled via process step (b) into process step (a), and the pentenenitrile components which may be present in stream 4 depending on the distillation conditions are preferably removed from stream 4 by recycling stream 4 into the distillation apparatus of process step (b) and only the 1,3-butadiene and butene isomers fraction of stream 4 is ultimately recycled into step (a) via stream 2.

In process step (c), in addition to stream 4, a further stream 5 is obtained which is recovered at a side draw of the column. This stream 5 comprises 3-pentenenitrile and 2-methyl-3-butenenitrile, in addition to other pentenenitrile isomers and residual constituents of 1,3-butadiene and butene isomers. The proportion of 3-pentenenitrile and 2-methyl-3-butenenitrile in stream 5 is a total of preferably from 80 to 100% by weight, more preferably from 85 to 99.998% by weight, in particular from 90 to 99.9% by weight, based in each case on stream 5. The proportion of 1,3-butadiene and butene isomers in stream 5 is preferably from 0 to 20% by weight, more preferably from 10 ppm by weight to 5% by weight, in particular from 50 ppm by weight to 2% by weight, based in each case on stream 5. Stream 5 is preferably withdrawn in vaporous form.

The side draw of the distillation apparatus is preferably disposed below the feed point of stream 3, more preferably in a position corresponding to from 1 to 20, in particular from 2 to 10, distillative separation stages below the feed point of stream 3.

The bottom product obtained in process step (c) is a stream 6 which comprises the at least one catalyst, and also trans-3-pentenenitrile and 2-methyl-3-butenenitrile. The proportion of pentenenitrile isomers in stream 6 is a total of preferably from 0.1 to 80% by weight, more preferably from 5 to 50% by weight, in particular from 10 to 40% by weight, based in each case on stream 6.

Particular preference is given to at least partly recycling stream 6 into process step (a) of the hydrocyanation, and a regeneration is as described in DE-A-103 51 002. In a further embodiment of the process according to the invention, the distillation unit of process step (c) may be operated with one or more further liquid or vaporous side draws, above or below the feed point of stream 3, in order to withdraw discharge or recycle streams.

In addition, it is also possible to fully or partly use stream 6 from process step (c) as a catalyst stream for other hydrocyanations, for example for hydrocyanating 3-pentenenitrile. When catalyst stream 6 is used for hydrocyanating 3-pentenenitrile, it is preferred that the content of 2-methyl-3-butenenitrile in this catalyst stream 6 is very low.

In a preferred embodiment of the process according to the invention in process step (c), the position of the side draw and the total number of theoretical plates of the distillation apparatus in process step (c) are selected in such a way that stream 6 is obtained via the bottom with a concentration of 2-methyl-3-butenenitrile which is lowered in comparison to stream 5, the lowering being based on the ratio of the concentrations of 2-methyl-3-butenenitrile to trans-3-pentenenitrile. Particular preference is given to from 1 to 50, in particular from 2 to 20, distillative separation stages between the position of the side draw and the bottom. This depletion of 2-methyl-3-butenenitrile may, if appropriate, also be effected in a separate apparatus designed as a distillation column with a stripping section. The proportion of 2-methyl-3-butenenitrile in the catalyst stream 6 is preferably from 0 to 5% by weight, more preferably from 10 ppm by weight to 2% by weight, in particular from 50 ppm by weight to 0.5% by weight, based on the catalyst stream 6. In a further embodiment of the process according to the invention, stream 6, after removal of a substream 6b for the purposes of discharge, regeneration or use in another hydrocyanation process, for example of 3-pentenenitrile to adiponitrile, may be supplemented by a stream of fresh catalyst in order to ensure the necessary amount of the at least one catalyst in process step (a). The fresh catalyst stream may stem from a selective synthesis, from a regeneration process or from a process for recovering the catalyst from a hydrocyanation process, especially from an extraction process step in a process for hydrocyanating 3-pentenenitrile to adiponitrile.

In a preferred embodiment, the fresh catalyst stream is fed either directly to process step (a) or to stream 6 downstream of the point where substream 6b was withdrawn.

In a further preferred embodiment, the fresh catalyst stream is conducted into the distillation apparatus of process step (c) in order to be able to control the pentenenitrile content of the entire catalyst stream to process step (a) within the abovementioned limits.

In a further preferred embodiment of the process according to the invention, the amount of catalyst discharge and thus the amount of fresh catalyst needed for supplementation is adjusted such that the content of methylglutaronitrile in the catalyst circulation is not above 50% by weight, more preferably not above 20% by weight, in particular not above 10% by weight, based in each case on the catalyst circulation, in order to have the particular catalyst stream discharged present in a regeneration with very minor inhibiting effects of methylglutaronitrile to the uptake of nickel(0).

In a further preferred embodiment of the process according to the invention, the amount of catalyst discharge and thus the amount of fresh catalyst needed for supplementation is adjusted such that the content of nickel(0) complexes in the catalyst circulation does not fall below 0.05% by weight, more preferably not below 0.1% by weight, in particular not below 0.2% by weight, based in each case on the catalyst circulation and calculated in each case as metallic nickel(0), in order to ensure the activity of the hydrocyanation catalyst despite losses of nickel(0) complexes during the reaction in step (a) or during the distillation process in step (b) and (c), preferably during the reaction in step (a).

In the process according to the invention, it is particularly preferred when stream 5 is obtained in vaporous form at the side draw in process step (c).

In a further preferred embodiment of the process according to the invention, it is possible to transfer stream 1 which is obtained in process step (a) directly into process step (c) with exclusion of process step (b).

Stream 5 is subsequently transferred to a further distillation apparatus in process step (d). In this distillation apparatus, stream 5 is distilled to obtain a stream 7 which comprises 2-methyl-3-butenenitrile, and a stream 8 which comprises 3-pentenenitrile. Stream 7 is obtained at the top of the distillation apparatus, while stream 8 is obtained in the bottom of the distillation apparatus.

In a particularly preferred embodiment of the process according to the invention, stream 5 which is in some cases obtained as a gaseous side draw is transferred in gaseous form to the distillation apparatus of process step (d), and the pressure at the position of the feed point for stream 5 in the distillation apparatus of process step (d) is less than or equal to the pressure at the position of the side draw for stream 5 in the distillation apparatus of process step (c).

Not excluded from the scope of this description are process variants in which the pressure of stage (d) is selected freely and gas stream 5 is, if appropriate, compressed to a higher pressure than at the withdrawal point in (c), in order to be fed to stage (d).

Process step (d) of the process according to the invention may be carried out in any suitable apparatus known to those skilled in the art. Suitable apparatus for this distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in one apparatus.

The columns preferably contain structured packings. The structured packings preferably generate from 5 to 100, more preferably from 10 to 80, in particular from 15 to 50, theoretical plates.

The pressure in process step (d) is preferably from 0.001 to 100 bar, more preferably from 0.01 to 20 bar, in particular from 0.05 to 2 bar. The distillation is carried out in such a way that the temperature in the bottom of the distillation apparatus is preferably from 30 to 250° C., more preferably from 50 to 200° C., in particular from 60 to 180° C. The distillation is carried out in such a way that the condensation temperature at the top of the distillation apparatus is preferably from −50 to 250° C., more preferably from 0 to 180° C., in particular from 15 to 160° C. In a particularly preferred embodiment of the process according to the invention, the aforementioned temperature ranges are maintained both at the top and in the bottom of the distillation apparatus.

In one embodiment of the process according to the invention, stream 7 which is obtained in process step (d) is recycled into process step (a) and/or into process step (b), and the reaction conditions in process step (a) or the residence time of the liquid phase in the bottom of process step (b) are selected in such a way that 2-methyl-3-butenenitrile is at least partly isomerized to trans-3-pentenenitrile.

In a further embodiment of the process according to the invention, stream 7 is obtained as a side draw stream in the distillation apparatus of process step (d), and the top product of this distillation column which is obtained is a stream which, in addition to 2-methyl-3-butenenitrile, also comprises substantially (Z)-2-methyl-2-butenenitrile and in some cases 1,3-butadiene and butene isomers, and also vinylcyclohexene and ethylidenecyclohexene.

The content of trans-3-pentenenitrile in stream 7 is preferably from 0 to 50% by weight, more preferably from 100 ppm by weight to 20% by weight, in particular from 1 to 15% by weight. The content of 2-methyl-3-butenenitrile in stream 8 is preferably from 0 to 10% by weight, more preferably from 5 ppm by weight to 5% by weight, in particular from 50 ppm by weight to 1% by weight.

The process according to the invention enables the preparation of 3-pentenenitrile and 2-methyl-3-butenenitrile in an integrated process which, owing to the recycling, possible to a virtually full extent, of the 1,3-butadiene streams and the catalyst stream, has a high process yield for the feedstocks. The temperatures and pressure conditions needed for the distillative removal of 1,3-butadiene and pentenenitrile isomers from the catalyst streams can be selected in such a way that firstly the bottom evaporator temperatures when the process is practiced on the production scale with industrially achieveable residence times are so low that they preferentially do not lead to catalyst damage, and that secondly the condensation of the top products of the particular distillation steps preferentially takes place at temperatures at which the heat removal on the production scale is possible with economically acceptable cost.

One embodiment of the process according to the invention is illustrated in detail with reference to FIG. 1.

FIG. 1 shows a schematic of one embodiment of the process according to the invention. Into reactor R1 are introduced 1,3-butadiene (BD), hydrogen cyanide (HCN) and a homogeneous nickel(0) catalyst (CAT). In this reactor, a hydrocyanation of 1,3-butadiene takes place. This forms stream 1 which comprises substantially 3-pentenenitrile, 2-methyl-3-butenenitrile, the nickel(0) catalyst, 1,3-butadiene and hydrogen cyanide. This stream is subsequently transferred to a distillation column K1. Here, a separation of stream 1 takes place into a stream 2 which comprises 1,3-butadiene and is recycled into reactor R1, and into a stream 3 which comprises 3-pentenenitrile, the nickel(0) catalyst and 2-methyl-3-butenenitrile.

Stream 3 is subsequently transferred to a second distillation column K2. Here, the residual 1,3-butadiene (stream 4) is removed from stream 3 via the top of the column, which is recycled into column K1, and also the catalyst is removed with a stream 6 from the bottom of the column, which is depleted in 3-pentenenitrile and 2-methyl-3-butenenitrile. Stream 6 is recycled into reactor R1. At a side draw of column K2, a stream 5 is obtained. This stream 5 comprises 3-pentenenitrile and 2-methyl-3-butenenitrile. Stream 4 is recycled into K1.

The stream 5 is subsequently transferred to a third distillation column K3. Here, a separation is effected into stream 8 which comprises 3-pentenenitrile and is withdrawn at the bottom of the column, and stream 7 which comprises 2-methyl-3-butenenitrile and is withdrawn at the top of the distillation column.

Stream 8 which comprises 3-pentenenitrile may be fed to a further hydrocyanation to adiponitrile.

The present invention is illustrated in detail with reference to the working examples which follow.

In the examples, the following abbreviations are used:
HCN: hydrogen cyanide
CAT: catalyst
BD: 1,3-butadiene
REG: regeneration stage

EXAMPLE 1

Figure 2:
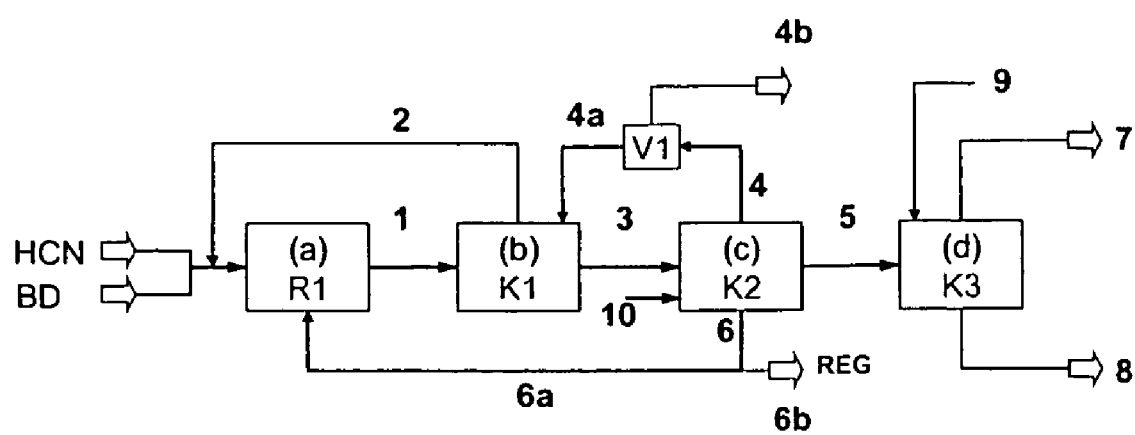

Example 1 is illustrated with reference to FIG. 2.

In Example 1, a catalyst system based on nickel(0) complexes with a mixture of ligands is used for the hydrocyanation of 1,3-butadiene. The ligand mixture for the hydrocyanation contains approx 60 mol % of tri(m/p-tolyl) phosphite and 40 mol % of the chelate phosphonite 1:

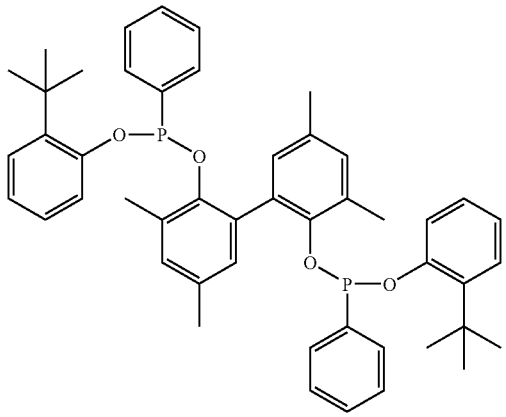

In a process step (a), the following streams are conducted into a loop reactor R1 of capacity 25 l which is equipped with a nozzle, impulse exchange tube, external pumped circulation and a heat exchanger disposed in the pumped circulation system to remove the energy of the reaction, and is heated at 357 K:

(1) 10 kg/h of liquid, unstabilized hydrogen cyanide freed of water by distillation;

(2) 22 kg/h of commercial tert-butylpyrocatechol-stabilized 1,3-butadiene containing 0.25% by weight of cis-2-butene, the 1,3-butadiene having been treated by contact with alumina in order to remove water and the stabilizer;

(3) 8 kg/h of recycled 1,3-butadiene from column K1 of process step (b) (stream 2), so that the entire 1,3-butadiene feed to reactor R1 which is obtained is a stream of 30 kg/h containing 90% by weight of 1,3-butadiene, 5% by weight of cis-2-butene and 5% by weight of 1-butene;

(4) 21 kg/h of nickel(0) catalyst solution, obtained as described below in this example, as stream 6a from column (K2) of process step (c).

The stream 1 drawn off from reactor R1 (63 kg/h) contains a total of 11% by weight of 1,3-butadiene and cis-2-butene, corresponding to a conversion of 79% of 1,3-butadiene, and also a total of 63% by weight of pentenenitriles, 31% by weight of trans-3-pentenenitrile, 29% by weight of 2-methyl-3-butenenitrile, minor amounts of cis-3-pentenenitrile, trans-2-pentenenitrile, cis-2-pentenenitrile, 4-pentenenitrile and small amounts of (Z)-2-methyl-2-butenenitrile and (E)-2-methyl-2-butenenitrile, and also the catalyst constituents and catalyst degradation products and methylglutaronitrile.

In process step (b), stream 1 is fed to a distillation column K1 which is operated with rectifying and stripping section, and is equipped with a falling-film evaporator and divided column bottom, and also column internals having structured packing which generate 10 theoretical plates. Column K1 is operated at the top with a direct condenser which consists of a column section equipped with structured packing and having a total collecting cup, pumped circulation and external heat exchanger. Column K1 is operated at an absolute pressure of 2.0 bar top pressure, top temperature 288 K and bottom draw temperature 363 K.

Via the top of column K1 is obtained stream 2 which, as described at the outset, is metered as a recycle stream into reactor R1. The reflux ratio at the top of column K1 is adjusted in such a way that stream 2 contains approx. 100 ppm of 2-methyl-3-butenenitrile.

Via the bottom of column K1 are obtained 59 kg/h of a stream 3 which contains 2.9% by weight of 1,3-butadiene, 4.6% by weight of cis-2-butene, 67% by weight of pentenenitriles, and also additionally the catalyst constituents. cis-2-Butene is distinctly enriched in relation to 1,3-butadiene compared to the feed.

In a process step (c), stream 3 is conducted into a distillation column K2 which is operated in stripping mode and is equipped with a falling-film evaporator, top condenser with postcondenser, and also column internals having structured packing which generate 10 theoretical plates. The column is operated at an absolute pressure of 150 mbar top pressure, top temperature 329 K and bottom draw temperature 373 K. The vapor stream of the column is partly condensed at 308 K and treated at 263 K with a postcondenser. The stream 4 thus depleted of 2-methyl-3-butenenitrile and other pentenenitriles is compressed in a compressor V1 to an absolute pressure of 1.2 bar. The compressed gas stream is condensed at 279 K for the most part to obtain a stream 4a (5 kg/h), and a substream 4b (approx. 50 l (STP)/h, containing 44% by weight of cis-2-butene) is disposed of in gaseous form. Stream 4a is recycled in liquid form into the reflux section of the divided column bottom of column K1.

In a gaseous side draw of column K2 is obtained stream 5 (40 kg/h) containing approx. 50 ppm of 1,3-butadiene, 46% by weight of 2-methyl-3-butenenitrile and 48% by weight of trans-3-pentenenitrile, and also, to a lesser extent, (E)-2-methyl-2-butenenitrile and (Z)-2-methyl-2-butenenitrile in addition to other pentenenitrile isomers. The position of the side draw is selected in such a way that the 2-methyl-3-butenenitrile component in the stream 6 obtained via the bottom is depleted below the side draw in a stripping section in relation to trans-3-pentenenitrile.

In addition to stream 3, 13 kg/h of a catalyst stream (stream 10) are conducted into column K2 containing a total of 73% by weight of pentenenitriles, 0.5% by weight of Ni(0), 18% by weight of ligand mixture and approx. 5% by weight of adiponitrile.

Via the bottom of column K2 is obtained the catalyst stream 6 containing 0.5% by weight of Ni(0), approx. 100 ppm of 2-methyl-3-butenenitrile and 35% by weight of residual pentenenitriles. Stream 6 is partly (stream 6a) recycled into reactor R1 (21 kg/h). Another portion (stream 6b: 5.4 kg/h) is fed to a regeneration (REG) in order, after the regeneration, to be used, for example, in Example 1 of the hydrocyanation of 3-pentenenitrile according to DE-A-102 004 004 683.

In a process step (d), stream 5 is conducted to a distillation column K3 which is equipped with circulation evaporator and top condenser, and also with a structured packing which generates 30 theoretical plates. Column K3 is operated at an absolute pressure of 180 mbar top pressure, top temperature 345 K and bottom draw temperature 363 K.

39 kg/h of a stream 9 are conducted into column K3, containing 54% by weight of trans-3-pentenenitrile, 23% by weight of 2-methyl-3-butenenitrile and 16% by weight of (Z)-2-methyl-2-butenenitrile, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 1 of DE-A-102 004 004 671.

Via the top of column K3 are obtained 40 kg/h of a stream 7 containing 10% by weight of trans-3-pentenenitrile, 68% by weight of 2-methyl-3-butenenitrile, 16% by weight of (Z)-2- methyl-2-butenenitrile, and also a total of 0.1% by weight of 1,3-butadiene and cis-2-butene. This stream may be fed to a process for isomerizing 2-methyl-3-butenenitrile to 3-pentenenitrile, as described in Example 1 of DE-A-102 004 004 671.

Via the bottom of column K3 are obtained 39 kg/h of stream 8 containing a total of 97% by weight of trans-3-pentenenitrile, cis-3-pentenenitrile and 4-pentenenitrile, and also approx. 100 ppm of 2-methyl-3-butenenitrile and approx. 1% by weight of (E)-2-methyl-2-butenenitrile.

Example 1 shows how virtually full recovery of butadiene and catalyst is possible in a hydrocyanation process. In Example 1, the catalyst is removed in two stages in column K1 and column K2 under gentle conditions, and the nitrile stream can be recovered in column K2 substantially free of butadiene.

The composition, found in Example 1, of the recovered catalyst stream is particularly suitable for use in a process for hydrocyanating pentenenitrile to adipodinitrile, since stream 6 and thus also stream 6b are obtained substantially free of 2-methyl-3-butenenitrile and butadiene.

EXAMPLE 2

Figure 3:
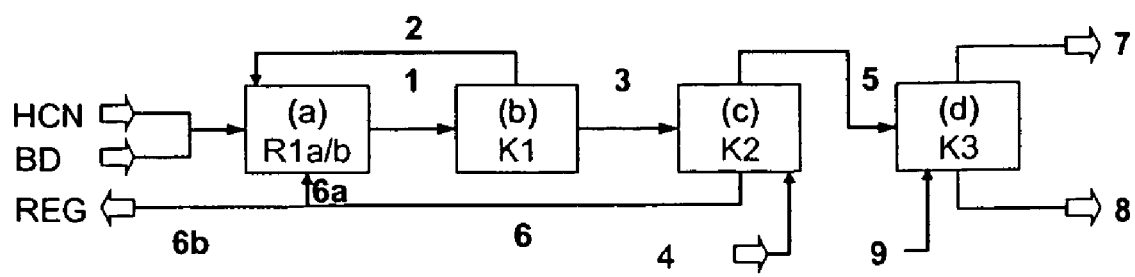

Example 2 is illustrated with reference to FIG. 3.

In Example 2, a catalyst system based on nickel(0) complexes with chelate phosphite 2 as the ligand is used for the hydrocyanation of 1,3-butadiene:

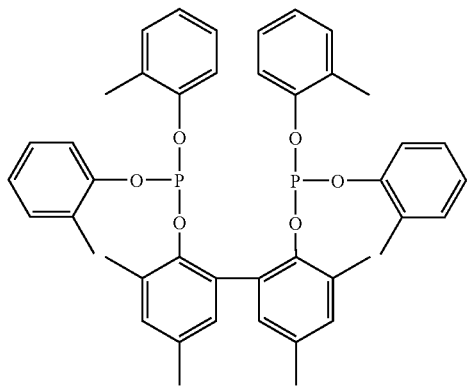

In a process step (a), the following streams are conducted into a system composed of two reactors R1a and R1b, each of capacity 12 l, and each of which is equipped with a nozzle, impulse exchange tube, external pumped circulation and a heat exchanger disposed in the pumped circulation system for removing the energy of reaction, and heated at 363 K:
 (1) 6 kg/h of liquid, unstabilized hydrogen cyanide freed of water by distillation to R1a;
 (2) 6 kg/h of liquid, unstabilized hydrogen cyanide freed of water by distillation to R1b;
 (3) 25 kg/h of commercial 1,3-butadiene to R1a, containing 0.25% by weight of cis-2-butene, the 1,3-butadiene having been treated by contact with alumina in order to remove water and the stabilizer;
 (4) 2 kg/h of recycled 1,3-butadiene from column K1 in process step (b) to R1a (stream 2), so that the entire 1,3-butadiene feed to reactor R1 which is obtained is a stream of 27 kg/h containing 98% by weight of 1,3-butadiene and a total of 2% by weight of cis-2-butene and 1-butene;
 (5) 14 kg/h of nickel(0) catalyst solution to R1a, obtained as described below in this example as stream 6a from column (K2) of process step (c).

The stream 1 drawn off from reactor R1b (54 kg/h) contains a total of 4% by weight of 1,3-butadiene and cis-2-butene, corresponding to a conversion of 94% of 1,3-butadiene, and also a total of 74% by weight of pentenenitriles, of which 33% by weight is trans-3-pentenenitrile, 37% by weight is 2-methyl-3-butenenitrile, minor amounts are cis-3-pentenenitrile, trans-2-pentenenitrile, cis-2-pentenenitrile, 4-pentenenitrile and small amounts are (Z)-2-methyl-2-butenenitrile and (E)-2-methyl-2-butenenitrile, and also the catalyst constituents and catalyst degradation products and methylglutaronitrile.

In a process step (b), stream 1 is fed to a distillation column K1 which is operated as a rectifying column and is equipped with a falling-film evaporator and also column internals having structured packing which generate 4 theoretical plates. Column K1 is operated at the top with a direct condenser which consists of a column section equipped with random packing and having total collecting cup, pumped circulation and external heat exchanger. Column K1 is operated at an absolute pressure of 0.8 bar top pressure, top temperature 263 K and bottom draw temperature 393 K.

Via the top of column K1 is obtained stream 2 which, as described at the outset, is metered into the reactor R1a as a recycle stream. The reflux ratio at the top of column K1 is adjusted in such a way that stream 2 contains 0.1% by weight of 2-methyl-3-butenenitrile.

Via the bottom of column K1 are obtained 52 kg/h of a stream 3 which contains 0.3% by weight of 1,3-butadiene, 0.1% by weight of cis-2-butene, 76% by weight of pentenenitriles, and also additionally the catalyst constituents.

In process step (c), stream 3 is conducted into a distillation column K2 which is operated in stripping mode and is equipped with a falling-film evaporator, top condenser with postcondenser, and also with column internals having structured packing which generate 4 theoretical plates. The column is operated at an absolute pressure of 70 mbar top pressure, top temperature 333 K and a bottom draw temperature 373 K.

At the gaseous top draw of column K2 is obtained stream 5 (40 kg/h) containing 0.4% by weight of 1,3-butadiene, 54% by weight of 2-methyl-3-butenenitrile and 42% by weight of trans-3-pentenenitrile, and also to a lesser extent, (E)-2-methyl-2-butenenitrile and (Z)-2-methyl-2-butenenitrile in addition to other pentenenitrile isomers.

3 kg/h of a catalyst stream (stream 4) are conducted into column K2, containing a total of 45% by weight of pentenenitriles, 1.5% by weight of Ni(0) and the chelate ligand, obtained, for example, by reacting nickel(0)(cyclooctadienyl)$_2$ complex with the chelate phosphite 2.

Via the bottom of column K2 is obtained the catalyst stream 6 containing 1.2% by weight of Ni(0), 0.3% by weight of 2-methyl-3-butenenitrile and 17% by weight of residual pentenenitriles. Stream 6 is partly (stream 6a) recycled into reactor R1 (14 kg/h). Another portion (stream 6b: 3.8 kg/h) is fed to a regeneration (REG) and may, after the regeneration (REG), for example, be used in the hydrocyanation of 3-pentenenitrile or, if appropriate, be recycled into the hydrocyanation of 1,3-butadiene by the process according to the invention.

In a process step (d), stream 5 is conducted to a distillation column K3 which is equipped with circulation evaporator and top condenser, and also with a structured packing which generates 45 theoretical plates. Column K3 is operated at an absolute pressure of 1.0 bar top pressure, top temperature 395 K and bottom draw temperature 416 K.

24 kg/h of recycle stream 9 are fed into column K3, containing 70% by weight of trans-3-pentenenitrile, 14% by weight of 2-methyl-3-butenenitrile and 7% by weight of (Z)-2-methyl-2-butenenitrile, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 2 of DE-A-102 004 004 671.

Via the top of column K3 are obtained 30 kg/h of a stream 7 containing 1% by weight of trans-3-pentenenitrile, 85% by weight of 2-methyl-3-butenenitrile, 8% by weight of (Z)-2-methyl-2-butenenitrile, and also a total of 3% by weight of 1,3-butadiene and cis-2-butene. The reflux ratio of column K3 is adjusted in such a way that 1% by weight of 3-pentenenitrile is obtained overhead. This stream may, for example, be fed to a process for isomerizing 2-methyl-3-butenenitrile to 3-pentenenitrile, as described in Example 2 of DE-A-102 004 004 671.

Via the bottom of column K3 are obtained 38 kg/h of stream 8 containing a total of 97% by weight of trans-3-pentenenitrile, cis-3-pentenenitrile, trans-2-pentenenitrile, cis-2-pentenenitrile and 4-pentenenitrile, and also approx. 10 ppm of 2-methyl-3-butenenitrile and approx. 2% by weight of (E)-2-methyl-2-butenenitrile and small amounts of methylglutaronitrile. Stream 8 may be fed to a process for hydrocyanating 3-pentenenitrile to adiponitrile, as described in Example 2 of DE-A-102 004 004 683.

In Example 2, stream 6 is obtained in column K2, and thus also stream 6b without the separation stages in question, with a noticeable proportion of 2-methyl-3-butenenitrile (approx. 1.5% by weight based on the nitrile content of the catalyst stream in Example 2 instead of approx. 0.1% by weight in Example 1), which leads to a noticeable loss in product of value by formation of methylglutaronitrile when this catalyst, after the regeneration, is used to hydrocyanate 3-pentenenitrile to adiponitrile.

EXAMPLE 3

Figure 4:
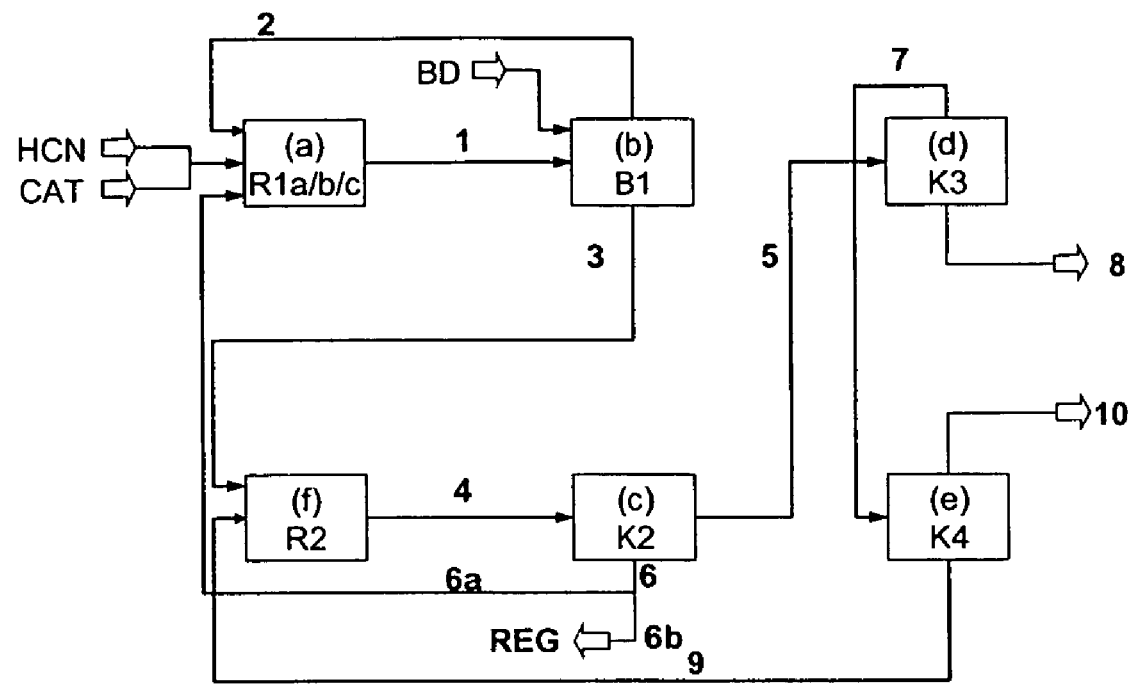

Example 3 is illustrated with reference to FIG. 4.

In Example 3, a catalyst system based on nickel(0) complexes with a mixture of ligands is used for the hydrocyanation of 1,3-butadiene. The ligand mixture for the hydrocyanation contains approx. 80 mol % of tri(m/p-tolyl) phosphite and 20 mol % of the chelate phosphite 2.

In a process step (a), the following streams are conducted into a system composed of three continuous stirred tanks R1a, R1b and R1c connected in series, each of capacity 10 l, which are heated to 373 K:

(1) 5.2 kg/h of liquid, unstabilized hydrogen cyanide freed of water by distillation to R1a;
(2) 4.0 kg/h of liquid, unstabilized hydrogen cyanide freed of water by distillation to R1b;
(3) 23 kg/h of 1,3-butadiene as stream 2 from the condenser of the evaporator B1 in process step (b), containing 92% by weight of 1,3-butadiene, 2% by weight of trans-3-pentenenitrile, 4% by weight of 2-methyl-3-butenenitrile and approx. 2% by weight of cis-2-butene to R1a;
(4) 4.1 kg/h of nickel(0) catalyst solution to R1a, obtained as described below in this example, as stream 6a from rectification column K2 in process step (c);
(5) 3.7 kg/h of nickel(0) catalyst solution to R1a (CAT), containing a total of 45% by weight of pentenenitriles, 1.1% by weight of Ni(0), 38% by weight ligand mixture and approx. 12% by weight of adiponitrile.

Reactor R1c is operated at 353 K as a postreactor with the effluent from reactor R1b.

The stream 1 withdrawn from reactor R1c (37 kg/h) contains 7% by weight of 1,3-butadiene, corresponding to a conversion of 86% 1,3-butadiene, and also a total of 77% by weight of pentenenitriles, of which 33% by weight is trans-3-pentenenitrile, 41% by weight is 2-methyl-3-butenenitrile, minor amounts are cis-3-pentenenitrile, trans-2-pentenenitrile, cis-2-pentenenitrile, 4-pentenenitrile, and small amounts are (Z)-2-methyl-2-butenenitrile and (E)-2-methyl-2-butenenitrile, and also the catalyst constituents, catalyst degradation products and methylglutaronitrile.

In a process step (b), stream 1 is fed to an evaporator stage B1 which is equipped with a circulation evaporator. The evaporator stage B1 is operated at the top with a condenser which is flushed with condensed material from the reflux vessel. The evaporator stage B1 is operated at an absolute pressure of 0.5 bar top pressure, condensation temperature 253 K and bottom draw temperature 363 K.

18.5 kg/h of commercial 1,3-butadiene are metered into the condensate collecting vessel of evaporator stage B1, containing 0.25% by weight of cis-2-butene, which has been treated by contact with molecular sieve, the water content of the 1,3-butadiene used having been reduced to less than 10 ppm by weight of $H_2O$.

From the condensate collecting vessel of the evaporator stage B1, stream 2 is drawn off as the sum of recycled and freshly metered 1,3-butadiene and recycled to reactor R1a as described above.

Via the bottom of evaporator stage B1 are obtained 37 kg/h of a stream 3 which contains a total of 1% by weight of 1,3-butadiene and cis-2-butene, 82% by weight of pentenenitriles and also additionally the catalyst constituents.

In a process step (f), stream 3 is conducted into a reactor R2, heated at 383 K and designed as a stirred tank with downstream delay zone, and 2-methyl-3-butenenitrile is isomerized to trans-3-pentenenitrile in the presence of the nickel catalyst and of a Lewis acid.

A pentenenitrile recycle stream 9 is conducted into reactor R2 (10 kg/h) which is obtained as the bottom product in column 4 in process step (e), containing 60% by weight of 2-methyl-3-butenenitrile, a total of 10% by weight of trans-3-pentenenitrile with further pentenenitrile isomers, and also vinylcyclohexene and small amounts of 1,3-butadiene.

From reactor R2, a stream 4 is obtained (45 kg/h), containing 62% by weight of trans-3-pentenenitrile and 14% by weight of 2-methyl-3-butenenitrile, corresponding to a conversion of 70% by weight of 2-methyl-3-butenenitrile to trans-3-pentenenitrile, and also the catalyst components.

In a process step (c), stream 4 is conducted into a rectification column K2 which is equipped with a falling-film evaporator and condenser and is operated as a stripping column at an absolute pressure of 50 mbar and bottom draw temperature 393 K with column internals which make available 10 distillative separation stages.

From the condenser of the rectification column K2, a stream 5 is obtained (38 kg/h), containing 91% by weight of pentenenitrile isomers and also approx. 1% by weight of 1,3-butadiene and, to a lesser extent, (E)-2-methyl-2-butenenitrile, (Z)-2-methyl-2-butenenitrile and vinylcyclohexene.

Via the bottom of rectification column K2 is obtained the catalyst stream 6 (7 kg/h), containing 1.3% by weight of Ni(0), approx. 20 ppm of 2-methyl-3-butenenitrile, 17% by weight of residual pentenenitriles, the residual catalyst constituents, adiponitrile and methylglutaronitrile. Stream 6 is partly (stream 6a) recycled into reactor R1 (4.4 kg/h). The remainder (stream 6b) may be fed to a regeneration (REG), and subsequently used, for example, in a hydrocyanation of 3-pentenenitrile (according to US 2003/0100442 or according to DE-A-103 51 002). In addition, the catalyst may be reused in the process according to the invention for hydrocyanating 1,3-butadiene, if appropriate after removal of zinc chloride.

In a process step (d), stream 5 is conducted to a distillation column K3 which is equipped with forced circulation evaporator and top condenser, and also with column internals which generate 30 theoretical plates. Column K3 is operated at an absolute pressure of 0.12 bar top pressure, top temperature 334 K and bottom draw temperature 352 K.

Via the top of column K3 are obtained 10 kg/h of a stream 7 containing 5% by weight of trans-3-pentenenitrile, 60% by weight of 2-methyl-3-butenenitrile, 4% by weight of (Z)-2-methyl-2-butenenitrile, and also a total of 4% by weight of 1,3-butadiene and cis-2-butene. The reflux ratio of column K3 is adjusted in such a way that 5% by weight of 3-pentenenitrile is obtained overhead.

Via the bottom of column K3 are obtained 27 kg/h of stream 8 containing a total of 98% by weight of trans-3-pentenenitrile, cis-3-pentenenitrile and 4-pentenenitrile, and also approx. 1000 ppm of 2-methyl-3-butenenitrile and approx. 2% by weight of (E)-2-methyl-2-butenenitrile.

In a process step (e), stream 7 is conducted into a distillation column K4 which is operated as a rectifying column and is equipped with forced circulation evaporator, top condenser, reflux divider, and also column internals having structured packing which generate 15 theoretical plates. Column K4 is operated at an absolute pressure of 380 mbar top pressure, top temperature 361 K and bottom draw temperature 365 K.

In column K4, a liquid stream 10 is obtained overhead (0.6 kg/h), containing a total of 4% by weight of 1,3-butadiene and cis-2-butene, 54% by weight of 2-methyl-3-butenenitrile, 38% by weight of (Z)-2-methyl-2-butenenitrile and 2.5% by weight of vinylcyclohexene. The amount of stream 10 drawn off from the top of column K4 is adjusted in such a way that the top draw stream 7 of column K3 contains a total of 30% by weight of (Z)-2-methyl-2-butenenitrile and vinylcyclohexene. In column K4, a gaseous stream is obtained at the top condenser operated as a partial condenser (195 1 (STP)/h) which comprises substantially 1,3-butadiene.

In column K4, stream 9 is obtained via the bottom (9.4 kg/h) and, in addition to 3-pentenenitriles, comprises substantially the 2-methyl-3-butenenitrile unconverted in the isomerization and is recycled in step (f) into the isomerization reactor R2.

In Example 3, the distillation apparatus K1 from Example 1 is designed as a single-stage evaporation B1, which leads, in comparison to Example 1, to a distinctly higher concentration of nitriles, especially 2-methyl-3-butenenitrile, in the recycled butadiene and to higher butadiene losses.

EXAMPLE 4

Figure 5:
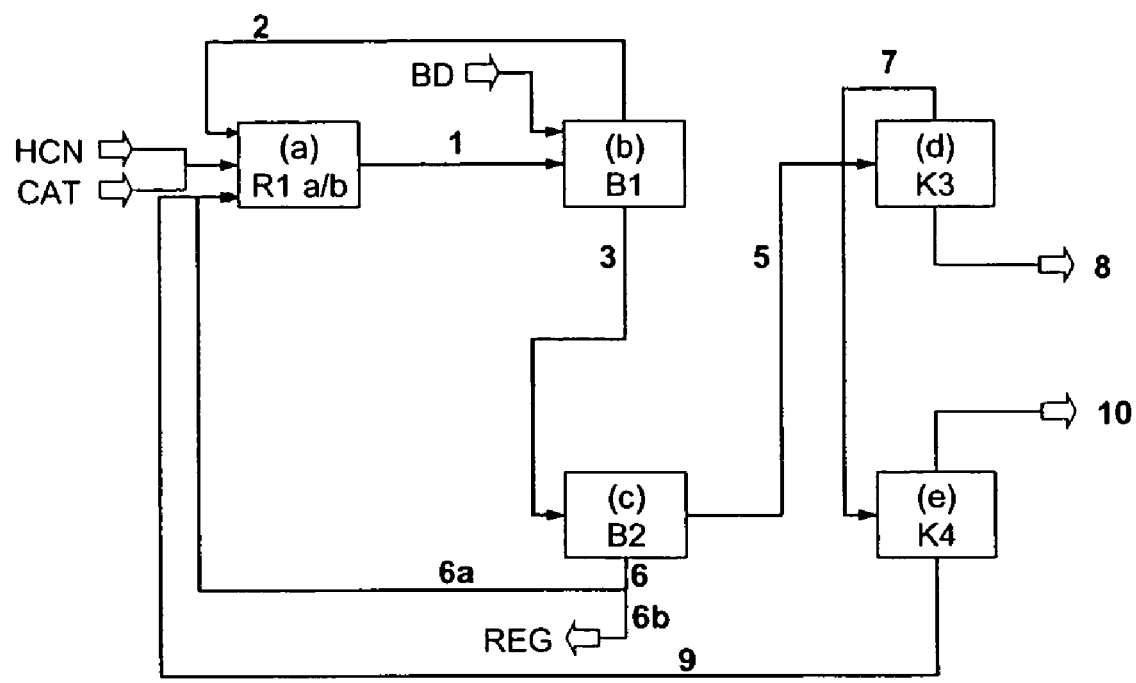

Example 4 is illustrated with reference to FIG. 5.

In Example 4, a catalyst system based on nickel(0) complexes with a mixture of ligands is used for the hydrocyanation of 1,3-butadiene. The ligand mixture for the hydrocyanation contains approx. 80 mol % of tri(m/p-tolyl) phosphite and 20 mol % of the chelate phosphonite 1.

In a process step (a), the following streams are conducted into a system composed of two continuous stirred tanks R1a and R1b connected in series, each of capacity 50 l, which are heated to 363 K:

(1) 18 kg/h of liquid, unstabilized hydrogen cyanide freed of water by distillation in equal parts to reactors R1a and R1b,
(2) 62 kg/h of 1,3-butadiene as stream 2 from the top of the evaporator B1 in process step (b), containing 87% by weight of 1,3-butadiene, 3% by weight of trans-3-pentenenitrile, 6% by weight of 2-methyl-3-butenenitrile and approx. 2% by weight of cis-2-butene to reactor R1a,
(3) 61 kg/h of nickel(0) catalyst solution, obtained as described below in this example, as stream 6a from the evaporator stage B2 in process step (c) to reactor R1a,
(4) 6.7 kg/h of nickel(0) catalyst solution to R1a (CAT), obtained as described in Example 1 of DE-A-102 004 004 683, as the bottom draw of column K4 from process step (4) of Example 2 of this patent application, containing a total of 45% by weight of pentenenitriles, 1.1% by weight of Ni(0), 38% by weight of ligand mixture and approx. 12% by weight of adiponitrile to reactor R1a, the 1,3-butadiene stream and the catalyst stream being premixed before contacting with hydrogen cyanide,
(5) 29 kg/h of a nitrile recycle stream 9 obtained as the bottom draw of column K4 as described below in the example, containing 19% by weight of trans-3-pentenenitrile, 62% by weight of 2-methyl-3-butenenitrile, further nitriles and vinylcyclohexene.

The stream 1 drawn off from reactor R1b (177 kg/h) contains 11% by weight of 1,3-butadiene, corresponding to a conversion of 66% 1,3-butadiene, and also a total of 64% by weight of pentenenitriles, of which 32% by weight is trans-3-pentenenitrile, 30% by weight is 2-methyl-3-butenenitrile, minor amounts are cis-3-pentenenitrile, trans-2-pentenenitrile, cis-2-pentenenitrile, 4-pentenenitrile, and small amounts are (Z)-2-methyl-2-butenenitrile and (E)-2-methyl-2-butenenitrile, and also the catalyst constituents and catalyst degradation products.

In a process step (b), stream 1 is fed to an evaporator stage B1 which is equipped with a falling-film evaporator. Evaporator stage B1 is operated at the top with a condenser which is flushed with condensed material from the reflux vessel. Evaporator stage B1 is operated at an absolute pressure of 1.3 bar top pressure, condensation temperature 278 K and bottom draw temperature 403 K.

37 kg/h of commercial 1,3-butadiene are metered into the condensate collecting vessel of evaporator stage B1, containing 0.25% by weight of cis-2-butene which has been treated by contact with molecular sieve, the water content of the 1,3-butadiene used having been reduced to less than 5 ppm by weight and the tert-butylpyrocatechol stabilizer present in the 1,3-butadiene used getting into the condensate collecting vessel and the condenser flushing circuit in concentrations on the ppm scale.

From the condensate collecting vessel of the evaporator stage B1, stream 2 is drawn off as the sum of recycled and freshly metered 1,3-butadiene and recycled to reactor R1a as described above.

Via the bottom of evaporator stage B1 are obtained 152 kg/h of a stream 3 which contains 0.9% by weight of 1,3-butadiene, 16% by weight of 2-methyl-3-butenenitrile, 51% by weight of trans-3-pentenenitrile and further pentenenitrile isomers, and also additionally the catalyst constituents. The composition of the bottom effluent of the evaporator stage allows a degree of conversion of 50% by weight of 2-methyl-3-butenenitrile to trans-3-pentenenitrile in the bottom of the evaporator to be concluded.

In a process step (c), stream 3 is conducted into an evaporator stage B2 which is equipped with a falling-film evaporator and condenser and is operated at an absolute pressure of 260 mbar and bottom draw temperature 383 K.

From the evaporator stage B2, a stream 5 is obtained in gaseous form (83 kg/h), containing 93% by weight of pentenenitrile isomers, approx. 1% by weight of 1,3-butadiene and, to a lesser extent, (E)-2-methyl-2-butenenitrile, (Z)-2-methyl-2-butenenitrile and vinylcyclohexene. Stream 5 is conducted into distillation column K3 in process step (d).

Via the bottom of the evaporator stage B2 is obtained the catalyst stream 6 (69 kg/h), containing 0.6% by weight of Ni(0), 2% by weight of 2-methyl-3-butenenitrile and 42% by weight of residual pentenenitriles. Stream 6 is for the most part (stream 6a) recycled into reactor R1 (61.4 kg/h). The remaining (stream 6b) is fed to a regeneration (REG), for example according to DE-A-103 51 002, and can be used in the hydrocyanation of 3-pentenenitrile, for example according to DE-A-102 004 004.

In a process step (d), stream 5 is conducted in gaseous form to a distillation column K3 which is equipped with a forced circulation flash evaporator and top condenser, and also with a structured packing which generates 30 theoretical plates. Column K3 is operated at an absolute pressure of 80 mbar top pressure, top temperature 375 K and bottom draw temperature 343 K.

Via the top of column K3 are obtained 36 kg/h of a stream 7 containing 15% by weight of trans-3-pentenenitrile, 64% by weight of 2-methyl-3-butenenitrile, 3% by weight of (Z)-2-methyl-2-butenenitrile, and also a total of 4% by weight of 1,3-butadiene and cis-2-butene. The reflux ratio of column K3 is adjusted in such a way that 15% by weight of trans-3-pentenenitrile is obtained overhead.

Via the bottom of column K3 are obtained 47 kg/h of stream 8 containing a total of 98% by weight of trans-3-pentenenitrile, cis-3-pentenenitrile, trans-2-pentenenitrile, cis-2-pentenenitrile and 4-pentenenitrile, and also 100 ppm of 2-methyl-3-butenenitrile and approx. 1% by weight (E)-2-methyl-2-butenenitrile.

In a process step (e) stream 7 is conducted into a distillation column K4 which is operated as a rectifying column and is equipped with a forced circulation evaporator, top condenser, reflux divider, and also column internals having structured packing which generate 45 theoretical plates. The column is operated at an absolute top pressure of 320 mbar, condensation temperature 288 K and bottom draw temperature 363 K.

In this column K4, a liquid stream 10 is obtained overhead (6.8 kg/h), containing a total of 10% by weight of 1,3-butadiene and cis-2-butene, 80% by weight of 2-methyl-3-butenenitrile, 8% by weight of (Z)-2-methyl-2-butenenitrile, and 0.5% by weight of vinylcyclohexene. In column K4, a gaseous stream is obtained at the top condenser operated as a partial condenser (approx. 250 l (STP)/h) which comprises substantially 1,3-butadiene.

In column K4, stream 9 is obtained via the bottom (28.7 kg/h) and, in addition to 3-pentenenitriles, comprises substantially 2-methyl-3-butenenitrile unconverted in the isomerization, and is recycled into the hydrocyanation reactor R1.

In Example 4, both the distillation apparatus K1 and the distillation apparatus K2 from Example 1 are each designed as single-stage evaporator stages B1 and B2, which leads, in comparison to Example 1, even when the conditions in stage B1 are adapted, to noticeable butadiene losses, and the catalyst stream is more highly thermally stressed than in Example 1.

EXAMPLE 5

Figure 6:
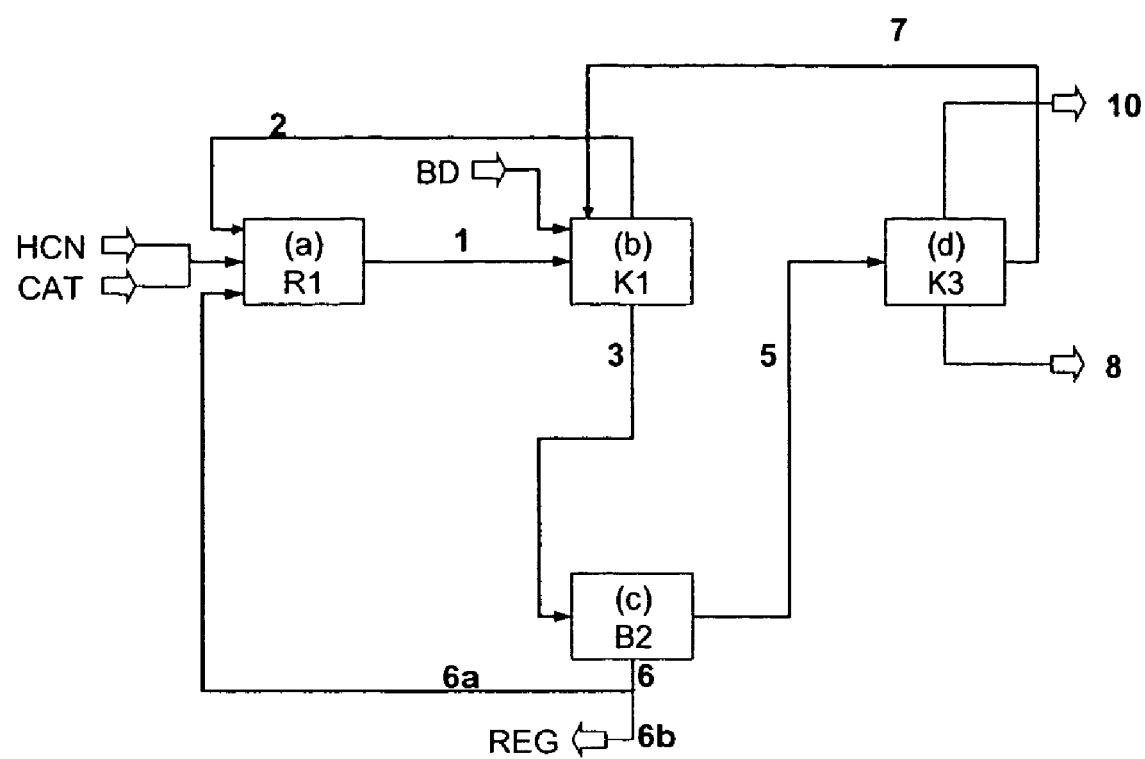

Example 5 is illustrated with reference to FIG. 6.

In Example 5, a catalyst system based on nickel(0) complexes with chelate phosphonite 1 as a ligand is used for the hydrocyanation of 1,3-butadiene.

In a process step (a), the following streams are conducted into a a continuous stirred tank R1 of capacity 30 l which is heated to 363 K:
  (1) 16 kg/h of liquid, unstabilized hydrogen cyanide freed of water by distillation,
  (2) 50 kg/h of 1,3-butadiene as stream 2 from the top of evaporator B1 in process step (b), containing 94% by weight of 1,3-butadiene, 2% by weight of trans-3-pentenenitrile, 4% by weight of 2-methyl-3-butenenitrile and approx. 1% by weight of cis-2-butene,
  (3) 10 kg/h of nickel(0) catalyst solution, obtained as described below in this example as stream 6a from evaporator stage B2 in process step (c), containing a total of 42% by weight of pentenenitriles, 23% by weight of ligand, 0.9% by weight of nickel(0), and also in each case approx. 10% by weight of adiponitrile and methylglutaronitrile,
  (4) 4 kg/h of nickel(0) catalyst solution to R1 (CAT), containing a total of 45% by weight of pentenenitriles, 1.5% by weight of Ni(0) and 48% by weight of ligand.

The stream 1 drawn off from reactor R1 (89 kg/h) contains 17% by weight of 1,3-butadiene, corresponding to a conversion of 71% 1,3-butadiene, and also a total of 73% by weight of pentenenitriles, of which 32% by weight is trans-3-pentenenitrile, 36% by weight is 2-methyl-3-butenenitrile, minor amounts are cis-3-pentenenitrile, trans-2-pentenenitrile, cis-2-pentenenitrile, 4-pentenenitrile, and small amounts are (Z)-2-methyl-2-butenenitrile and (E)-2-methyl-2-butenenitrile, and also the catalyst constituents and catalyst degradation products.

In a process step (b), stream 1 is fed to a distillation column K1 which is equipped with a falling-film evaporator and is operated as a stripping column with column internals which make available 8 distillative separation stages. The distillation column K1 is operated at the top with a condenser which is flushed with condensed material from the reflux vessel. The distillation column K1 is operated at an absolute pressure of 1.3 bar top pressure, condensation temperature 278 K and bottom draw temperature 403 K.

The nitrile recycle stream 7 from column K3, as described below, is recycled into the distillation column K1.

34 kg/h of commercial 1,3-butadiene are metered into the condensate collecting vessel of distillation column K1, containing 0.25% by weight of cis-2-butene, which has been treated by contact with alumina, the water content of the 1,3-butadiene used having been reduced to less than 10 ppm by weight of $H_2O$ and the content of tert-butylpyrocatechol stabilizer to less than 10 ppm.

From the condensate collecting vessel of the evaporator stage, stream 2 is drawn off as the sum of recycled and freshly metered 1,3-butadiene, and recycled to reactor R1a as described above.

Via the bottom of distillation column K1 are obtained 76 kg/h of a stream 3 which contains 0.8% by weight of 1,3-butadiene, 12% by weight of 2-methyl-3-butenenitrile, 69% by weight of trans-3-pentenenitrile and further pentenenitrile isomers, and also additionally the catalyst constituents. The composition of the bottom effluent of the evaporator stage corresponds to a degree of conversion of 75% by weight of 2-methyl-3-butenenitrile to trans-3-pentenenitrile in the bottom of the evaporator stage K1.

In a process step (c), stream 3 is conducted into an evaporator stage B2 which is equipped with a falling-film evaporator and condenser, and is operated at an absolute pressure of 220 mbar and bottom draw temperature 381 K.

From the evaporator stage B2, a stream 5 is obtained in gaseous form (58 kg/h), containing 97% by weight of pentenenitrile isomers, and also approx. 1% by weight of 1,3-butadiene and, to a lesser extent, (E)-2-methyl-2-butenenitrile, (Z)-2-methyl-2-butenenitrile and vinylcyclohexene.

Via the bottom of evaporator stage B2 is obtained the catalyst stream 6 (17 kg/h) containing 0.9% by weight of Ni(0), 0.3% by weight of 2-methyl-3-butenenitrile and 42% by weight of residual pentenenitriles. Stream 6 is for the most part (stream 6a) recycled into reactor R1 (10 kg/h). The remainder (stream 6b) is fed to a regeneration (REG), for example according to US 2003/0100442 and may, after regeneration, be used in a hydrocyanation of 3-pentenenitrile, or be recycled into the process according to the invention, into the process step for hydrocyanating 1,3-butadiene.

Stream 5 is condensed and conducted in liquid form in a process step (d) to a distillation column K3 which is equipped with forced circulation evaporator and top condenser, and also with structured packing which generates 50 theoretical plates. Column K3 is operated at an absolute pressure of 0.200 bar top pressure, top temperature 342 K and bottom draw temperature 366 K.

At the top of column K3 is obtained a stream 10 containing 10% by weight of 1,3-butadiene, 18% by weight of (Z)-2-methyl-2-butenenitrile, 68% by weight of 2-methyl-3-butenenitrile, and also further pentenenitrile isomers and vinylcyclohexenes. The reflux ratio of column K3 is adjusted in such a way that the top draw stream contains 18% by weight of (Z)-2-methyl-2-butenenitrile.

At a liquid side draw of column K3 are obtained 8 kg/h of a stream 7 containing 0.5% by weight of trans-3-pentenenitrile, 85% by weight of 2-methyl-3-butenenitrile, 5% by weight of (Z)-2-methyl-2-butenenitrile and 10% by weight of vinylcyclohexene. Stream 7 is recycled into the distillation column K1 in step (b).

Via the bottom of column K3 are obtained 47 kg/h of stream 8 containing a total of 98% by weight of trans-3-pentenenitrile, cis-3-pentenenitrile and 4-pentenenitrile, and also 100 ppm of 2-methyl-3-butenenitrile and approx. 1% by weight of (E)-2-methyl-2-butenenitrile.

In Example 5, the distillation apparatus K1 from Example 1 is designed as a distillation column with stripping section; the distillation apparatus K2 from Example 1 may be designed here as a single-stage evaporation B2, since the 2-methyl-3-butenenitrile content in the feed to B2 is distinctly reduced by preceding isomerization in comparison to Examples 1, 2 or 3. In comparison to Example 4, the procedure according to Example 5 leads to lower butadiene losses, but the catalyst stream is still more highly contaminated than in Example 1 or 2.

What is claimed is:

1. A process for preparing 3-pentenenitrile, characterized by the following process steps:
    (a) reacting 1,3-butadiene with hydrogen cyanide over at least one catalyst to obtain a stream 1 which comprises 3-pentenenitrile, 2-methyl-3-butenenitrile, the at least one homogeneously dissolved nickel(0) catalyst which is stabilized with phosphorus ligands and the phosphorus ligands are selected from the group consisting of phosphines, phosphites, phosphinites and phosphonites, and 1,3-butadiene,
    (b) distilling stream 1 in a column to obtain a high-1,3-butadiene stream 2 as the top product and a low-1,3-butadiene stream 3 as the bottom product which comprises 3-pentenenitrile, the at least one catalyst and 2-methyl-3-butenenitrile,
    (c) distilling stream 3 in a column to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst,
    (d) distilling stream 5 to obtain a stream 7 as the top product which comprises 2-methyl-3-butenenitrile, and a stream 8 as the bottom product which comprises 3-pentenenitrile,
    with the proviso that, in process steps (b) and (c), the bottom temperatures do not exceed 140° C. and the sum of the average residence times in the distillation apparatus in process steps (b) and (c) together is not more than 10 hours.

2. The process according to claim 1, wherein the high-1,3-butadiene stream 2 from process step (b) is recycled at least partly into process step (a).

3. The process according to claim 1, wherein, in process step (c), stream 6 is obtained via the bottom with a concentration of 2-methyl-3-butenenitrile which is lowered in comparison to stream 5, the lowering being based on the ratio of the concentrations of 2-methyl-3-butenenitrile to trans-3-pentenenitrile.

4. The process according to claim 1, wherein stream 6 from process step (c) is recycled at least partly into process step (a).

5. The process according to claim 1, wherein stream 4 from process step (c) is recycled at least partly into process step (a) and/or (b).

6. The process according to claim 1, wherein stream 5 is withdrawn in vaporous form at the side draw in process step (c).

7. The process according to claim 1, wherein stream 7 from process step (d) is recycled at least partly into process step (a) and/or process step (b).

8. The process according to claim 1, wherein, in process step (c), there are from 1 to 50 distillative separation stages between the position of the side draw and the column bottom.

9. The process according to claim 1, wherein the proportion of 2-methyl-3-butenenitrile in the catalyst stream 6 obtained in process step (c) is from 0 to 5% by weight.

10. The process according to claim 2, wherein, in process step (c), stream 6 is obtained via the bottom with a concentration of 2-methyl-3-butenenitrile which is lowered in comparison to stream 5, the lowering being based on the ratio of the concentrations of 2-methyl-3-butenenitrile to trans-3-pentenenitrile.

11. The process according to claim 10, wherein stream 6 from process step (c) is recycled at least partly into process step (a).

12. The process according to claim 11, wherein stream 4 from process step (c) is recycled at least partly into process step (a) and/or (b), wherein stream 5 is withdrawn in vaporous form at the side draw in process step (c), wherein stream 7 from process step (d) is recycled at least partly into process step (a) and/or process step (b), wherein, in process step (c), there are from 1 to 50 distillative separation stages between the position of the side draw and the column bottom, and wherein the proportion of 2-methyl-3-butenenitrile in the catalyst stream 6 obtained in process step (c) is from 0 to 5% by weight.

13. The process according to claim 2, wherein stream 6 from process step (c) is recycled at least partly into process step (a).

14. The process according to claim 2, wherein stream 4 from process step (c) is recycled at least partly into process step (a) and/or (b).

15. The process according to claim 2, wherein stream 5 is withdrawn in vaporous form at the side draw in process step (c).

16. The process according to claim 2, wherein stream 7 from process step (d) is recycled at least partly into process step (a) and/or process step (b).

17. The process according to claim 2, wherein, in process step (c), there are from 1 to 50 distillative separation stages between the position of the side draw and the column bottom.

18. The process according to claim 2, wherein the proportion of 2-methyl-3-butenenitrile in the catalyst stream 6 obtained in process step (c) is from 0 to 5% by weight.

19. The process according to claim 3, wherein stream 6 from process step (c) is recycled at least partly into process step (a).

20. The process according to claim 3, wherein stream 4 from process step (c) is recycled at least partly into process step (a) and/or (b).

* * * * *